(12) United States Patent
Vemulapalli et al.

(10) Patent No.: US 9,582,916 B2
(45) Date of Patent: Feb. 28, 2017

(54) METHOD AND SYSTEM FOR UNSUPERVISED CROSS-MODAL MEDICAL IMAGE SYNTHESIS

(71) Applicant: Siemens Healthcare GmbH, Erlangen (DE)

(72) Inventors: Raviteja Vemulapalli, Hyattsville, MD (US); Hien Nguyen, Bensalem, PA (US); Shaohua Kevin Zhou, Plainsboro, NJ (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 14/871,138

(22) Filed: Sep. 30, 2015

(65) Prior Publication Data

US 2016/0133037 A1 May 12, 2016

Related U.S. Application Data

(60) Provisional application No. 62/077,523, filed on Nov. 10, 2014.

(51) Int. Cl.
*G06K 9/00* (2006.01)
*G06T 11/60* (2006.01)
(Continued)

(52) U.S. Cl.
CPC ............ *G06T 11/60* (2013.01); *A61B 5/0035* (2013.01); *A61B 5/055* (2013.01); *A61B 5/7425* (2013.01); *G01R 33/50* (2013.01); *G01R 33/5602* (2013.01); *G01R 33/5608* (2013.01); *G06K 9/6244* (2013.01); *G06K 9/6289* (2013.01); *G06T 7/0012* (2013.01);
*A61B 5/0042* (2013.01); *A61B 2576/026* (2013.01); *G06K 2209/05* (2013.01); *G06T 2200/04* (2013.01);
(Continued)

(58) Field of Classification Search
CPC . G06T 11/60; G06T 2200/04; G06T 2200/32; G06T 2207/20212; G06T 2207/20021; G06T 2207/20081; G01R 33/5608; G01R 33/50; G01R 33/56; A61B 5/055; A61B 5/7425; A61B 5/0042; A61B 2576/026; A61B 5/0035; G06K 9/6244; G06K 9/6289; G06K 2209/05
USPC ........................................................ 382/128
See application file for complete search history.

(56) References Cited

U.S. PATENT DOCUMENTS 8,235,726 B2    8/2012   Hostettler et al.
8,241,041 B2    8/2012   Hostettler et al.
(Continued)

*Primary Examiner* — Gregory F Cunningham

(57) ABSTRACT

A method and apparatus for unsupervised cross-modal medical image synthesis is disclosed, which synthesizes a target modality medical image based on a source modality medical image without the need for paired source and target modality training data. A source modality medical image is received. Multiple candidate target modality intensity values are generated for each of a plurality of voxels of a target modality medical image based on corresponding voxels in the source modality medical image. A synthesized target modality medical image is generated by selecting, jointly for all of the plurality of voxels in the target modality medical image, intensity values from the multiple candidate target modality intensity values generated for each of the plurality of voxels. The synthesized target modality medical image can be refined using coupled sparse representation.

32 Claims, 4 Drawing Sheets

102

104

106

(51) Int. Cl.
 *G06T 7/00* (2006.01)
 *A61B 5/055* (2006.01)
 *A61B 5/00* (2006.01)
 *G01R 33/50* (2006.01)
 *G06K 9/62* (2006.01)
 *G01R 33/56* (2006.01)

(52) U.S. Cl.
 CPC  *G06T 2200/32* (2013.01); *G06T 2207/20021* (2013.01); *G06T 2207/20081* (2013.01); *G06T 2207/20212* (2013.01)

(56) References Cited

U.S. PATENT DOCUMENTS

| | | |
|---|---|---|
| 8,761,471 B2 | 6/2014 | Ozawa et al. |
| 2008/0037851 A1* | 2/2008 | Takayama ............... G06T 5/50 382/131 |
| 2008/0312884 A1* | 12/2008 | Hostettler ............... G06T 5/50 703/2 |
| 2009/0046912 A1* | 2/2009 | Hostettler ............ G09B 23/286 382/131 |
| 2012/0148139 A1 | 6/2012 | Ozawa et al. |
| 2013/0035583 A1 | 2/2013 | Park et al. |
| 2013/0259336 A1 | 10/2013 | Wakai |
| 2013/0342668 A1* | 12/2013 | Kasumi ............... H04N 5/772 348/74 |

\* cited by examiner

METHOD AND SYSTEM FOR UNSUPERVISED CROSS-MODAL MEDICAL IMAGE SYNTHESIS

This application claims the benefit of U.S. Provisional Application No. 62/077,523, filed Nov. 10, 2014, the disclosure of which is herein incorporated by reference.

BACKGROUND OF THE INVENTION

The present invention relates to synthesis of medical image data, and more particularly, to synthesizing subject-specific medical image data across image domains or image modalities.

A multitude of imaging modalities, such as X-ray, computed tomography (CT), diffuser tensor imaging (DTI), T1-weighted magnetic resonance imaging (MRI), T2-weighted MRI, etc., can be used for medical image analysis of a of a patient. Each of these imaging modalities captures different characteristics of the underlying anatomy and the relationship between any two modalities is highly nonlinear.

In many practical medical image analysis problems, a situation is often encountered in which medical image data available for training, for example for machine learning based anatomical object detection, has a different distribution or representation than the medical image data given during testing due to modality heterogeneity or domain variation. Due to variations in the image characteristics across modalities, medical image analyses algorithms trained with data from one modality may not work well when applied to medical image data from a different modality. A straightforward way to address this issue is to collect large amounts of training data from each imaging modality. However, this solution is impractical since collecting medical images is often time consuming and expensive.

Cross-modal synthesis generates medical images in a desired target modality from given source modality images. The ability to synthesize medical images without actual acquisition has many potential applications, such as atlas construction, multi-modal registration, super-resolution, and building virtual models. Various approaches for cross-modal synthesis have been proposed, but such approaches are either tailored to specific applications or work under a supervised setting in which training data from the same set of subjects in both the source and target modalities is required. Availability of such paired data is often limited and collecting such paired data is not desirable because each subject must be scanned multiple times. Accordingly, an unsupervised cross-modal medical image synthesis approach that generates target modality images without the need for paired training data is desirable.

BRIEF SUMMARY OF THE INVENTION

The present invention provides a method and system for unsupervised cross-modal synthesis of medical images. Embodiments of the present invention can be used with any pair of imaging modalities and do not require paired training data from the source and target modalities.

In one embodiment of the present invention, a source modality medical image is received. Multiple candidate target modality intensity values are generated for each of a plurality of voxels of a target modality medical image based on corresponding voxels in the source modality medical image. A synthesized target modality medical image is generated by selecting, jointly for all of the plurality of voxels in the target modality medical image, intensity values from the multiple candidate target modality intensity values generated for each of the plurality of voxels. The synthesized target modality medical image can be refined using coupled sparse representation.

These and other advantages of the invention will be apparent to those of ordinary skill in the art by reference to the following detailed description and the accompanying drawings.

DETAILED DESCRIPTION

The present invention relates to a method and system for unsupervised cross-modal synthesis of medical images. Embodiments of the present invention are described herein to give a visual understanding of the medical image synthesis method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
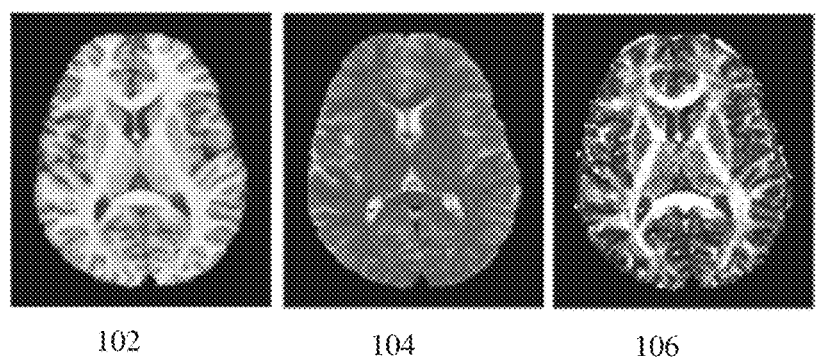
FIG. 1 illustrates images of the human brain in three different imaging modalities.

Embodiments of the present invention provide a generalized and robust framework for cross-modal synthesis of medical images. Embodiments of the present invention can be used to synthesize medical images in a target modality from available images in a source modality without having to perform image acquisition in the target modality. Embodiments of the present invention may be used to synthesize target modality medical images in order to create large training set of target modality medical images for training machine learning based classifiers for anatomical object detection, segmentation, tracking, and classification, without having to perform additional image acquisition on a large number of subjects. In addition, embodiments of the present invention may be used to synthesize target modality medical images for other applications, such as to create visualization tools for virtual domains, to perform cross-modality registration, or to up-sample the resolution of image data. As used herein, cross-model synthesis refers to synthesis of medical images across medical imaging modalities, such as synthesizing a CT image from an MR image, as well as synthesis of images across an image domain, such MR images with different protocols (e.g., T1 and T2), contrast CT images and non-contrast CT images, CT image captured with low kV and CT images captured with high kV, or any type of low resolution medical image to a corresponding high resolution medical image. That is, different modalities may refer to different domains or protocols within the same overall imaging modalities, and the "source modality" and "target modality" may be completely different medical imaging modalities or different image domains or protocols within the same overall imaging modality. FIG. 1 illustrates images of the human brain in three different imaging modalities. It is to be understood that the present invention is not limited to the above examples and may be performed to synthesize any type of target modality image from any type of source modality image.

Figure 2:
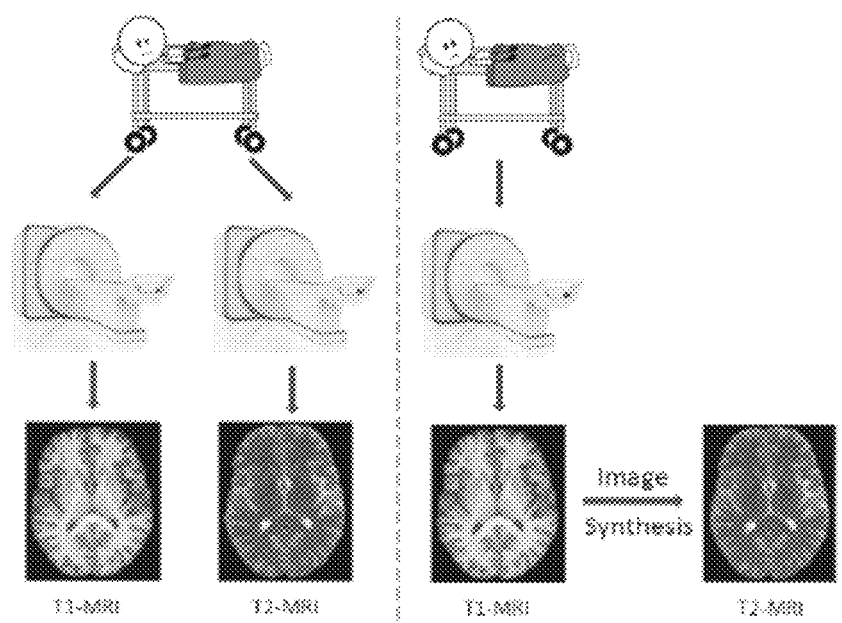
FIG. 2 illustrates an overview of cross-modal synthesis of medical images according to an embodiment of the present invention.

FIG. 1 illustrates images of the human brain in three different imaging modalities. As shown in FIG. 1, image 102 is a T1 MR image of the brain, image 104 is a T2 MR image of the brain, and image 106 is a diffusion tensor imaging-fractional anisotropy (DTI-FA) image of the brain. FIG. 2 illustrates an overview of cross-modal synthesis of medical images according to an embodiment of the present invention. In the exemplary embodiment of FIG. 2, cross-modal synthesis is used to synthesize a T2 MR image from an acquired T1 MR image. The left side (200) of FIG. 2 shows the acquisition of T1 and T2 MR images without using cross-modal synthesis. In this case, the patient must be scanned twice to acquire T1 and T2 MR images of the patient. The right side (210) of FIG. 2 shows the use of cross-modal synthesis to generate the T2 MR image. In this case, the patient is scanned once to acquire a T1 MR image (source modality image) and the T2 MR image (target modality image) is synthesized from the acquired T1 MR image.

Embodiments of the present invention provide a general fully-unsupervised method for cross-modal synthesis of subject-specific medical images. Embodiments of the present invention can be used with any pair of imaging modalities and do not require paired training data from the source and target imaging modalities. Since synthesizing a full medical image is a fairly complex task, embodiments of the present invention break this task into steps of candidate generation and candidate selection. Given a source modality image, multiple target modality candidate values are generated for each voxel using a cross-modal nearest neighbor search. The best candidate values are then selected for all the voxels jointly by solving an optimization problem that simultaneously maximizes a global mutual information cost function and minimizes a local spatial consistency cost function, resulting in a synthesized full target modality image. Coupled sparse representation can then be used to further refine the synthesized target modality image.

Figure 3:
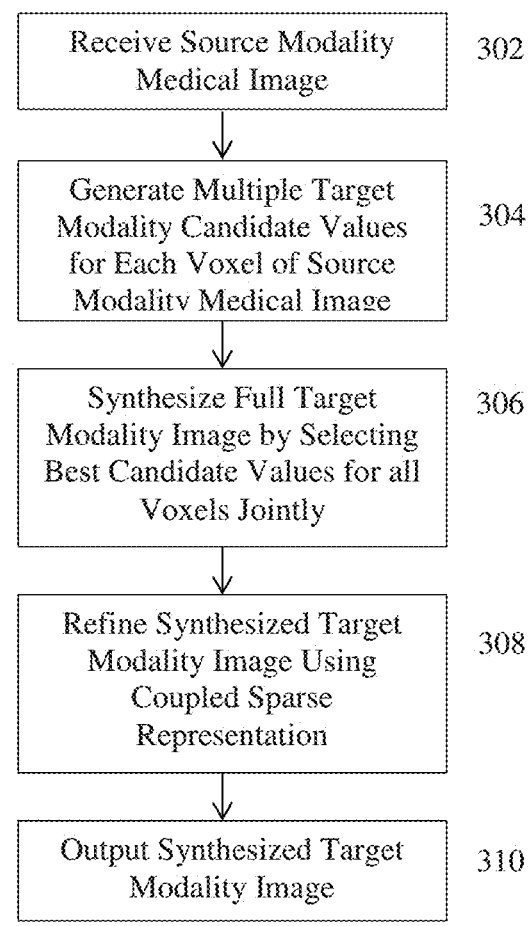
FIG. 3 illustrates a method for unsupervised cross-modal synthesis of medical images according to an embodiment of the present invention.

FIG. 3 illustrates a method for unsupervised cross-modal synthesis of medical images according to an embodiment of the present invention. The method of FIG. 3 transforms medical image data of a first modality (source modality) to generate a new medical image of a second modality (target modality). The method of FIG. 3 can be used for any type of cross-modal modality medical image synthesis, including but not limited to, synthesizing an MR image of one type of MR protocol (e.g., T2 MR image) from an MR image of another type of MR protocol (e.g., T1 MR image), synthesizing a contrast CT image from a non-contrast CT image, synthesizing a high-kV CT image from a low-kV CT image, synthesizing a high resolution medical image from a low resolution medical image of the same modality, synthesizing a CT image from an MR image, or for any other combination of imaging modalities (e.g. MR, CT, PET, DynaCT, etc.).

At step 302, a source modality medical image is received. The source modality medical image will also be referred to herein as the "source image". The source image can be acquired using any type of imaging modality, such as MR, CT, Ultrasound, X-ray fluoroscopy, DynaCT, positron emission tomography (PET), etc.

The medical image can be a 2D or 3D medical image. It is to be understood that although the medical image can be 2D or 3D, we use the term "voxel" herein to refer to elements of the medical image, regardless of the dimensionality of the medical image. In one possible implementation, the medical image can be a previously acquired medical image that is stored on a memory or storage of a computer system, or stored remotely on a server or other network device, and the medical image is received by loading the medical image to a computer system performing the method of FIG. 3. In another possible implementation, the medical image can be received directly from an image acquisition device, such as an MR scanner, CT scanner, etc.

At step 304, multiple candidate values for each voxel in the target modality medical image are generated based on the corresponding voxels in the source modality medical image. The target modality medical image will also be referred to herein as the "target image". Let $\Phi^v$ denote the set consisting of voxel v and its neighbors. In an advantageous implementation, the six voxels which are at a unit distance from v are used as neighbors. More neighbors can be added to the set $\Phi^v$ without significant changes to method described herein. We use the notation $\Phi^v(p,q,r)$ to represent the elements (voxels) of $\Phi^v$. Here, $\Phi^v(p,q,r)$ refers to the voxel $(v+(p,q,r))$. We represent the $l_0$ and $l_2$ norms using $\|\;\|_0$ and $\|\;\|_2$, respectively. The notation v~v' is used to indicate that the voxels v and v' are neighbors. We use II to denote the indicator function, which is equal to 1 when true and equal to 0 when false.

Given the source image $I_s$, multiple target modality candidate intensity values are generated for the respective set $\Phi^v$ representing the neighborhood at each voxel independently. To generate the target intensity values for $\Phi^v$, a $d_1 \times d_1 \times d_1$ patch centered on v is extracted from the received source modality medical image. If paired source-target images were available during training, it would be possible to learn a predictor/regressor to predict normal target modality candidate voxels for $\Phi^v$ from the source modality patch at voxel v. However, since such paired training data may not be available, embodiments of the present invention do not use such a trained predictor/regressor. In an advantageous embodiment of the present invention, a cross-modal nearest neighbor search is used to target modality candidate intensity values. For each $d_1 \times d_1 \times d_1$ image patch for the source image, K nearest $d_1 \times d_1 \times d_1$ target patches are obtained by searching across a set of target modality training images. In a possible implementation, K can be set equal 10, but the present invention is not limited to any particular value of K. The intensity values of the center voxel and the neighboring voxels from these K nearest image patches from the target modality training images provide the target modality candidate intensity values the set $\Phi^v$.

The cross-modal nearest neighbor search compares each patch of the source image with patches of the target modality training images using a similarity measure. The similarity measure should be robust to changes in modality. In an advantageous embodiment of the present invention, voxel-intensity based mutual information is used as the cross-modality similarity measure. Given two image patches A and B, their mutual information is given by:

$$MI(A,B)=H(X_a)+H(X_b)-H(X_a,X_b), \qquad (1)$$

where H denotes the Shannon entropy function, and $X_a$ and $X_b$ are random variables representing the voxel intensities in patches A and B, respectively. The mutual information similarity measure in Equation (1) measures the consistency between the intensity distributions of the image patches in the source and target domains. The Shannon entropy function is a well-known measure of entropy or uncertainty. $H(X_a)$ represents and uncertainty associated with the intensity value $X_a$ occurring in image patch A, $H(X_b)$ represents an uncertainty associated with the intensity value $X_b$ occurring in image patch B, and $H(X_a, X_b)$ represents an uncertainty associated with $X_a$ and $X_b$ occurring as intensity values of corresponding voxels in image patches A and B.

In order to generate the candidate target modality intensity values for the target image, a plurality of image patches are extracted from the source image. In a possible implementation, a respective patch can be centered at each voxel in the source image can be extracted. In another possible implementation, a predetermined number of voxels can be skipped in each direction between voxels at which the image patches are centered. In another possible implementation, the source image can be divided into a plurality of non-overlapping image patches that cover all of the voxels of the source image. Each image patch extracted from the source image is then compared with a large number of image patches of the target modality training images by calculating the mutual information similarity measure between the image patch of the source image and each image patch of the target modality training images, and K image patches of target modality training images having the highest mutual information similarity measure values are selected for each image patch of the source image. The intensity values for the center voxel. The intensity values of the center voxel and its neighboring voxels in each of the K image patches of the target modality training images selected for a particular source image are assigned to be candidate target modality intensity values for the voxels in the set $\Phi^v$ in the target image, where the voxel v in the target image is the voxel in the target image that corresponds to the center voxel of the image patch extracted from the source image (i.e., voxel v is located at the same location in the target image as the center voxel of the image patch is located in the source image). This results in a plurality of candidate target modality intensity values for each voxel in the target image.

Although the embodiment of the present invention described herein uses mutual information as a similarity measure, the present invention is not limited thereto and other cross-modality similarity measures can be used instead.

Returning to FIG. 3, at step 306, the full target modality medical image is synthesized by jointly selecting the best candidate values for all of the voxels in the target modality medical image. Given the K candidate target modality intensity values for the set $\Phi^v$ centered at each voxel in the target image, the full target modality medical image $I_t$ is synthesized by selecting one of the K candidates at each voxel. The value of $\Phi^v(0,0,0)$ (i.e., the intensity value of the center voxel) from the selected candidate is used to synthesize voxel v in $I_t$.

Let $X_s$ and $X_t$ be two random variables with support $\Psi = (l_1, l_2, \ldots, l_L)$, representing the voxel intensity values of the source and target images $I_s$ and $I_t$, respectively, where $l_1, l_2, \ldots, l_L$ are intensity values sampled from the intensity distribution of the source and target images $I_s$ and $I_t$. Let $I_s(v)$ and $I_t(v)$ denote the intensity values of voxel v in images $I_s$ and $I_t$, respectively. Let V represent the set of all voxels with cardinality $|V|=N$. Let $\{\phi^{v1}, \phi^{v2}, \ldots, \phi^{vK}\}$ denote the K candidate target modality intensity values for the set $\Phi^v$ at voxel v. Let $W_{vk} = II[\text{Candidate } \phi^{vk} \text{ is selected at voxel v}]$.

That is, $w_{vk}$ equals 1 when the candidate $\phi^{vk}$ is selected at voxel v and equals 0 when the candidate $\phi^{vk}$ is not selected at voxel v. In an advantageous embodiment of the present invention, since the candidates have been obtained for each voxel independently using the nearest neighbor search, the candidate intensity values are selected jointly for all of the voxels of the target image by solving a selection (optimization) problem based on the following two criteria: (i) Mutual information maximization, which is a global criterion; and (ii) Spatial consistency maximization, which is a local criterion.

It can be assumed that regions of similar tissue (and hence similar intensity values) in one image would correspond to regions in the other image that also have similar intensity values (though probably different values from the intensity values in the first image). Based on this assumption, mutual information is used as a cost function for cross-modal medical image synthesis. Since we are interested in generating synthesized subject specific scans, the synthesized target image $I_t$ should have high mutual information with the given source image $I_s$. That is the amount of information $I_s$ and $I_t$ contain about each other should be maximal. This global criterion helps in transferring the image level structure across modalities. The mutual information between images $I_s$ and $I_t$ is given by $MI(I_s, I_t) = H(X_s) + H(X_t) - M_s, X_t)$. Since the entropy $H(X_s)$ is constant for a given source image, maximizing mutual information is equivalent to maximizing $H(X_t) - H_s, X_t)$, where:

$$H(X_t) = -\sum_{b=1}^{L} P(X_t = l_b)\log[P(X_t = l_b)], \quad (2)$$

$$P(X_t = l_b) = \frac{1}{N}\sum_{v \in V}\sum_{k=1}^{K} w_{vk} II[\phi^{vk}(0,0,0) = l_b],$$

$$H(X_s, X_t) = -\sum_{a=1}^{L}\sum_{b=1}^{L} P_{ab}\log[P_{ab}],$$

$$P_{ab} =$$

$$P(X_s = l_a, X_t = l_b) = \frac{1}{N}\sum_{v \in V}\sum_{k=1}^{K} w_{vk} II[I_s(v) = l_a, \phi^{vk}(0,0,0) = l_b].$$

Regarding local spatial consistency maximization, let v, v' $\in$ V be two neighboring voxels of the target image. Note that if a candidate $\phi^{vi}$ is selected at voxel v, along with assigning the value $\phi^{vi}(0,0,0)$ to voxel v, the candidate $\phi^{vi}$ can also assign the value $\phi^{vi}(v'-v)$ to the neighboring voxel v'. Similarly, if a candidate $\phi^{v'j}$ is selected at voxel along with assigning the value $\phi^{v'j}(0,0,0)$ to voxel v', the candidate $\phi^{v'j}$ can also assign the value $\phi^{v'j}(v-v')$ to the neighboring voxel v. In this case, we would ideally like to have:

$$\phi^{vi}(0,0,0) = \phi^{v'j}(v-v'), \quad \phi^{v'j}(0,0,0) = \phi^{vi}(v'-v). \quad (3)$$

Hence, in an advantageous implementation, to promote spatial consistency among the selected candidate target modality intensity values, the following cost function can be minimized:

$$SC(W) = \sum_{\substack{v,v' \in V \\ v \sim v'}} [w_{v1} \ldots w_{vk}] \begin{bmatrix} C_{11}^{vv'} & \cdots & C_{1K}^{vv'} \\ \vdots & \ddots & \vdots \\ C_{K1}^{vv'} & \cdots & C_{KK}^{vv'} \end{bmatrix} \begin{bmatrix} W_{v'1} \\ \vdots \\ W_{v'K} \end{bmatrix}, \quad (4)$$

-continued where $$C_{ij}^{vv'} = \sqrt{\begin{array}{l}(\phi^{vi}(0, 0, 0) - \phi^{v'j}(v - v'))^2 + \\ (\phi^{v'j}(0, 0, 0) - \phi^{vi}(v' - v))^2\end{array}}.$$

According to an advantageous embodiment of the present invention, the global mutual information cost function and the spatial consistency cost function are combined into a single optimization problem. In particular, the selection of the candidate target modality intensity values for all of the voxels in the target image can be formulated as the following optimization problem:

$$\text{maximize}_{\{w_{vk}\}} H(X_t) - H(X_s, X_t) - \lambda SC(W) \quad (5)$$

$$\text{subject to } \sum_{k=1}^{K} w_{vk} = 1, \forall\, v \in V,$$

$$w_{vk} \in \{0, 1\}, \text{ for } k = 1, 2, \ldots, K, \forall\, v \in V,$$

where λ is a trade-off parameter.

The optimization problem in Equation (5) is combinatorial in nature due to binary integer constraints on $w_{vk}$ and is difficult to solve. In an advantageous implementation, the binary integer constraints are relaxed to positivity constraints to obtain the following relaxed optimization problem:

$$\text{maximize}_{\{w_{vk}\}} H(X_t) - H(X_s, X_t) - \lambda SC(W) \quad (6)$$

$$\text{subject to } \sum_{k=1}^{K} w_{vk} = 1, \forall\, v \in V,$$

$$w_{vk} \geq 0, \text{ for } k = 1, 2, \ldots, K, \forall\, v \in V,$$

The cost function $H(X_t) - H(X_s, X_t) - \lambda SC(W)$ is differentiable and its derivative with respect to $w_{vk}$ can be calculated using:

$$\frac{dH(X_t)}{dw_{vk}} = -\sum_{b=1}^{L} (1 + \log[P(X_t = l_b)]) \frac{d}{dw_{vk}} P(X_t = l_b) \quad (7)$$

$$= -\frac{1}{N}\sum_{b=1}^{L}(1 + \log[P(X_t = l_b)])II[\phi^{vk}(0, 0, 0) = l_b]$$

$$= -\frac{1}{N}(1 + \log[P(X_t = \phi^{vk}(0, 0, 0)]),$$

$$\frac{dH(X_s, X_t)}{dw_{vk}} = -\sum_{a=1}^{L}\sum_{b=1}^{L}(1 + \log[P_{ab}])\frac{dP_{ab}}{dw_{vk}}$$

$$= -\frac{1}{N}\sum_{a=1}^{L}\sum_{b=1}^{L}(1 + \log[P_{ab}])II[I_s(v) = l_a, \phi^{vk}(0, 0, 0) = l_b]$$

$$= -\frac{1}{N}(1 + \log[P(X_s = I_s(v), X_t = \phi^{vk}(0, 0, 0)]),$$

-continued $$\frac{dSC(W)}{sw_{vk}} = \sum_{v' \sim v}\left(\sum_{p=1}^{K} C_{kp}^{vv'} w_{v'p}\right).$$

The optimization problem in Equation (6) has a differentiable cost function with linear equality and equity constraints. Accordingly, in an exemplary implementation, this optimization problem can be solved using the reduced gradient ascent approach. Solving the optimization problem provides values for $w_{vk}$ for each candidate target modality intensity value for each voxel. In an advantageous implementation, the candidate $\phi^{vk*}$ is selected at each voxel v, where $k^* = \text{argmax}_k\, w_{vk}$. That is, since the binary constraint for $w_{vk}$ is relaxed in this optimization problem, the candidate with the maximum value for $w_{vk}$ is selected for each voxel. In an alternative implementation, a number of top candidates for each voxel having the highest values of $w_{vk}$ can be averaged to obtain the intensity value for each voxel of the target image.

Since the cost function in Equation (6) is non-convex, it is not guaranteed to find a global optimum. In an advantageous implementation, the local optimum obtained by initializing all of the variables $w_{vk}$ with a value of $$\frac{1}{K}$$

is used. This initialization can be interpreted as giving equal weight to all K candidates at the beginning of the optimization.

Returning to FIG. 3, at step 308, the synthesized target modality medical image is refined using coupled sparse representation. Sparse representation is a powerful model for image processing. Sparse representation models a signal as a linear combination of a small number of bases, also known as dictionary atoms: $x = D\alpha$, where $\|\alpha\|_0 \leq T_0$. Here, x is the signal, D is the dictionary whose columns are dictionary atoms, α is the sparse coefficient, and $\|\alpha\|_0$ is the number of non-zero elements which is constrained to be less than or equal to $T_0$, which is a predetermined threshold value. This representation can be regarded as a union of subspaces. The dictionary is typically not known a priori. The dictionary D can be learned (trained) to optimally represent the signal of interest using dictionary learning algorithms like K-SVD or method of orthogonal direction (MOD). Given a signal corrupted by different types of noise and a learned dictionary in which the signal can be sparsely represented, the original signal can be recovered using sparse coding techniques by finding the optimal sparse coefficient as $\alpha^* = \text{argmin}_\alpha \|x - D\alpha\|_2$, where $\|\alpha\|_0 \leq T_0$, wherein the recovered signal is reconstructed from the learned dictionary as $D\alpha^*$. In practice, sparse coding has been shown to perform well and yield superior reconstruction and noise reduction performance. This is due to the fact that random noises and artifacts are rarely sparse in the dictionary, which was learned to optimally represent the signal of interest.

Coupled sparse representation finds a coupled sparse code that best reconstructs that both of a pair of signals using respective dictionaries for the signals. To refine the synthesized target image using coupled sparse representation, at each voxel $v \in V$, small $d_2 \times d_2 \times d_2$ image patches are extracted from given source modality image $I_s$ and the synthesized target modality image $I_t$. Let $P_v^s$ and $P_v^t$ denote the patches centered at voxel v extracted from images $I_s$ and $I_t$, respectively. Using $\{((P_v^s, P_v^t)|v \in V)\}$ as signal pairs from the source and target modalities, coupled sparse representation can be formulated as the following optimization problem:

$$\text{minimize}_{D_s, D_t, \{\alpha_v\}} \sum_{v \in V} (\|P_v^s - D_s \alpha_v\|_2^2 + \|P_v^t - D_t \alpha_v\|_2^2) \quad (8)$$

$$\text{subject to } \|\alpha_v\|_0 \leq T_0 \; \forall \; v \in V,$$

where $D_s$ and $D_t$ are over-complete dictionaries with M atoms in the source and target modalities, respectively, $\alpha_v$ is the coupled sparse code for signals $P_v^s$ and $P_v^t$ in their respective dictionaries, and $T_0$ is the sparsity parameter.

The dictionaries $D_s$, $D_t$ and the coupled sparse codes $\alpha_v$ for each voxel are learned directly from the source image and the synthesized target image by the solving the optimization problem shown in Equation (8) using the K-SVD algorithm with explicitly re-normalizing the dictionary atoms of $D_s$ and $D_t$ separately to norm 1 after each iteration. Once the dictionaries and the coupled sparse codes for each voxel are learned from the source image and the synthesized target image, the target modality image patch $P_v^t$ is reconstructed at each voxel using the learned coupled sparse code $\alpha_v$ and the learned target modality dictionary $D_t$ as $\hat{P}_v^t = D_t \alpha_v$. The synthesized target image is refined by using the intensity value of the center voxel from $\hat{P}_v^t$ as the new target modality intensity value for voxel v.

Returning to FIG. 3, at step 310, the synthesized target modality image is output. For example, the synthesized target medical image can be displayed on a display of a computer system and/or stored in a storage or memory of a computer system.

Figure 4:
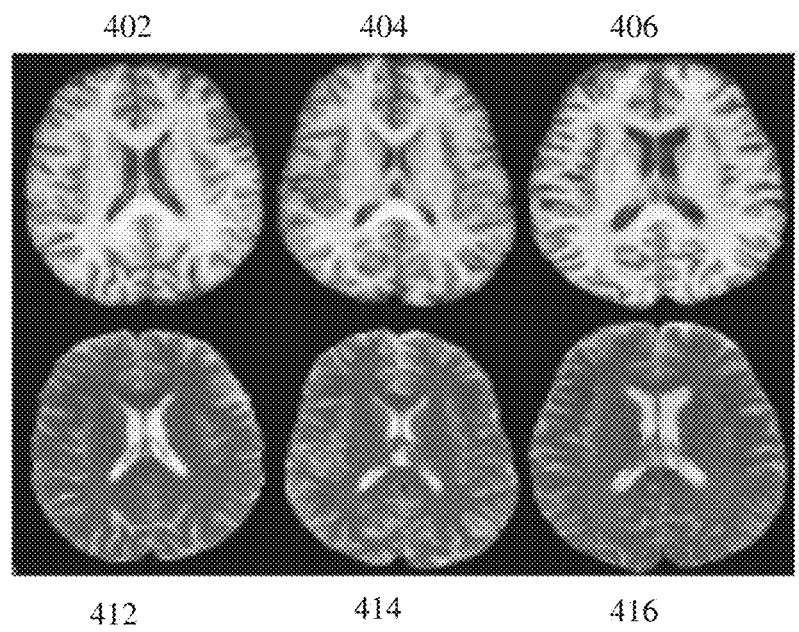
FIG. 4 illustrates corresponding T1-weighted MR brain images and T2-weighted MR brain images.

The method of FIG. 3 can be used to synthesize medical images across medical imaging modalities, as well as synthesis of images across an image domain. For example, the method of FIG. 3 can be used for applications including but not limited to synthesizing a CT image from an MR image, synthesizing an MR image with one protocol (e.g., T1 and T2) from an MR image with a different protocol, synthesizing contrast CT images from non-contrast CT images, synthesizing a high kV CT image from a low kV CT image, or synthesizing any type of high resolution medical image from a corresponding low resolution medical image. In an exemplary implementation, the present inventors have utilized the method of FIG. 3 to synthesize patient-specific T2-weighted MR brain images from T1-weighted MR brain images and vice versa. FIG. 4 illustrates corresponding T1-weighted MR brain images and T2-weighted MR brain images. As shown in FIG. 4, images 402, 404, and 406 are T1-weighted MR brain images of three different subjects and image 412, 414, and 416 are the respective corresponding T2-weighted MR brain images of the three different subjects.

In the present inventors experiments for synthesizing T2 MR brain images from T1 MR brain images and synthesizing T1 MR brain images from T2 MR brain images, the training images and the input source images were linearly registered, skull stripped, inhomogeneity corrected, histogram matched within each modality, and resampled to 2 mm resolution. Since the present inventors have access a database containing both T1-weighted and T2-weighted MR scans for a number of subjects, the synthesized images can be directly compared to ground truth target modality images for evaluation of the synthesis method. The present inventors utilized normalized cross-correlation as the evaluation metric.

Since exhaustively searching the target modality training images to find the nearest neighbors is highly computational, the search region in each target modality training image can be restricted to a h×h×h region surrounding the voxel in the target modality training image corresponding to the voxel of interest at which the image patch is centered in the source image. Since MR scans have a high dynamic range, a mutual information measure calculated using the original voxel intensity values may be highly unreliable. Accordingly, for computing the mutual information, the original voxel intensity values are quantized to L levels. The value trade-off $\lambda$ in the optimization problem expressed in Equation (6) was selected such that the values of the mutual information and spatial consistency costs are of the same order of magnitude. Exemplary parameters values that were used by the present inventors in the MR brain image synthesis experiments are shown in Table 1.

TABLE 1

Parameter values used in the experiments.

| Parameter | Description | Value |
|---|---|---|
| $d_1$ | Size of the image patch used for cross-modal nearest neighbor search | 9 |
| h | Size of the search region used for cross-modal nearest neighbor search | 7 |
| L | Number of quantization levels used for computing mutual information | 32 |
| K | Number of nearest neighbors | 10 |
| $d_2$ | Size of the image patch used for sparse representation | 3 |
| M | Number of dictionary atoms | 500 |
| $T_0$ | Sparsity parameter | 5 |
| $\lambda$ | Trade-off parameter in the optimization problem 6 | $10^{-8}$ |

Table 2 shows the normalized cross correlation values between the synthesized target modality images and the ground truth target modality images for 19 subjects. Based on results the MR brain image synthesis performed using the method of FIG. 3, it can be observed that target modality images synthesized using the method of FIG. 3 capture most of the structural information of ground truth target modality images. As shown in Table 2, synthesis of T1 images from T2 images produces more accurate results as compared to the synthesis of T2 images from T1 images. In addition, the results in Table 2 also show that coupled sparse representation (CSR) improves the synthesis results, in particular when synthesizing T2 images from T1 images.

TABLE 2

Normalized cross correlation values between synthe and ground truth target modality images.

| | Source: T1-MRI Target: T2-MRI | | Source: T2-MRI Target: T1-MRI | |
|---|---|---|---|---|
| Subject | No CSR | CSR | No CSR | CSR |
| 1 | 0.862 | 0.878 | 0.932 | 0.936 |
| 2 | 0.839 | 0.859 | 0.932 | 0.936 |
| 3 | 0.881 | 0.894 | 0.934 | 0.938 |
| 4 | 0.841 | 0.853 | 0.933 | 0.937 |
| 5 | 0.814 | 0.832 | 0.873 | 0.870 |
| 6 | 0.841 | 0.863 | 0.939 | 0.943 |
| 7 | 0.792 | 0.811 | 0.900 | 0.905 |

TABLE 2-continued

Normalized cross correlation values between synthe and ground truth target modality images.

| | Source: T1-MRI Target: T2-MRI | | Source: T2-MRI Target: T1-MRI | |
|---|---|---|---|---|
| Subject | No CSR | CSR | No CSR | CSR |
| 8 | 0.833 | 0.846 | 0.941 | 0.944 |
| 9 | 0.856 | 0.875 | 0.933 | 0.937 |
| 10 | 0.848 | 0.863 | 0.936 | 0.941 |
| 11 | 0.871 | 0.886 | 0.935 | 0.939 |
| 12 | 0.822 | 0.837 | 0.925 | 0.930 |
| 13 | 0.838 | 0.853 | 0.926 | 0.931 |
| 14 | 0.861 | 0.872 | 0.940 | 0.943 |
| 15 | 0.791 | 0.810 | 0.915 | 0.921 |
| 16 | 0.830 | 0.845 | 0.936 | 0.940 |
| 17 | 0.851 | 0.868 | 0.929 | 0.934 |
| 18 | 0.859 | 0.874 | 0.923 | 0.928 |
| 19 | 0.811 | 0.826 | 0.924 | 0.928 |
| average | 0.839 | 0.855 | 0.927 | 0.931 |

Embodiments of the present invention provide an unsupervised approach for cross-modal synthesis of subject specific medical images. The method described herein can be used with any pair of imaging modalities, and works without paired training data from the source and target modalities, thereby alleviating the need for scanning each subject multiple times. Given a source modality image, multiple candidate target modality intensity values are generated for each voxel location of a target modality image independently based on image patches extracted from the source modality image using a cross-modal nearest neighbor search. In an exemplary embodiment, voxel-intensity based mutual information is used as a similarity measure for the cross-modal nearest neighbor search, but the present invention is not limited thereto and other cross-modal similarity measures may be used as well. The best candidate values for all the voxels of the target modality image are selected jointly by simultaneously maximizing a global mutual interest cost and minimizing a local spatial consistency cost. Coupled sparse representation is used for further refinement of the synthesized target modality image.

Figure 5:
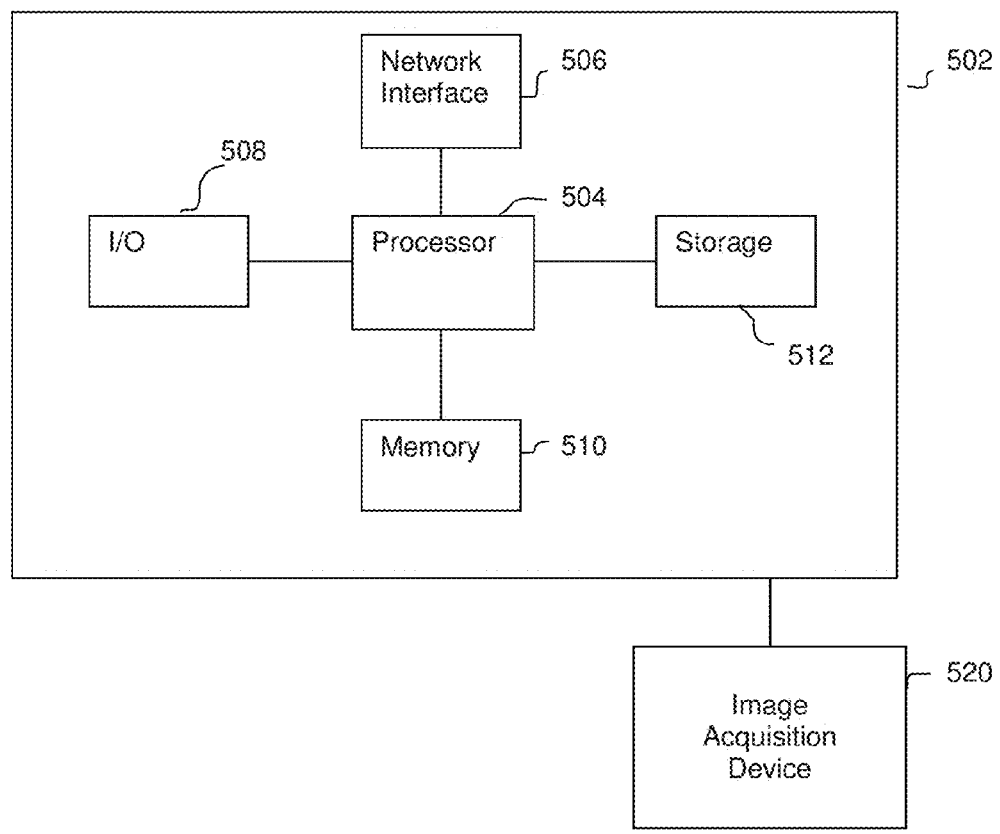
FIG. 5 is a high-level block diagram of a computer capable of implementing the present invention.

The above-described method for unsupervised cross-modal synthesis of medical images may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the method of FIG. 3 may be defined by the computer program instructions stored in the memory 510 and/or storage 512 and controlled by the processor 504 executing the computer program instructions. An image acquisition device 520, such as an MR scanning device or a CT scanning device, can be connected to the computer 502 to input image data to the computer 502. It is possible to implement the image acquisition device 520 and the computer 502 as one device. It is also possible that the image acquisition device 520 and the computer 502 communicate wirelessly through a network. In a possible embodiment, the computer 502 can be located remotely with respect to the image acquisition device 520 and the method steps described herein can be performed as part of a server or cloud based service. In this case, the method steps may be performed on a single computer or distributed between multiple networked computers. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for unsupervised cross-modal synthesis of a target modality medical image from a source modality medical image, comprising:
   receiving the source modality medical image;
   generating multiple candidate target modality intensity values for each of a plurality of voxels of the target modality medical image based on corresponding voxels in the source modality medical image; and
   generating a synthesized target modality medical image by selecting, jointly for all of the plurality of voxels in the target modality medical image, intensity values from the multiple candidate target modality intensity values generated for each of the plurality of voxels.

2. The method of claim 1, wherein generating multiple candidate target modality intensity values for each of a plurality of voxels of the target modality medical image based on corresponding voxels in the source modality medical image comprises:
   generating the multiple candidate target modality intensity values for each of the plurality of voxels independently using a cross-modal nearest neighbor search between a corresponding portion of the source modality medical image and a plurality of target modality training images.

3. The method of claim 1, wherein generating multiple candidate target modality intensity values for each of a plurality of voxels of the target modality medical image based on corresponding voxels in the source modality medical image comprises:
   extracting from the source modality medical image a plurality of image patches, each centered at a respective one of a plurality of voxels of the source modality medical image;
   obtaining, for each of the plurality of image patches extracted from the source modality medical image, K nearest image patches from a plurality of target modality training images using a cross-modal nearest neighbor search based on a cross-modal similarity measure between the image patches extracted from the source modality medical image and image patches of the target modality training images; and generating, for each of the plurality of image patches extracted from the source image, K candidate target modality intensity values for a corresponding set of voxels in the target modality medical image using intensity values of a corresponding set of voxels in each of the K nearest image patches from the plurality of target modality training images, wherein the corresponding set of voxels in the target modality medical image includes a voxel corresponding to the voxel at which the image patch extracted from the source image is centered and neighboring voxels and the corresponding set of voxels in each of the K nearest image patches includes a center voxel and neighboring voxels in each of the K nearest image patches.

4. The method of claim 3, wherein the cross-modal similarity measure between the image patches extracted from the source modality medical image and the image patches of the target modality training images is a voxel intensity-based mutual information measure.

5. The method of claim 4, wherein the voxel intensity-based mutual information measure between two image patches A and B is calculated as $MI(A,B)=H(X_a)+H(X_b)-H(X_a, X_b)$, where H denotes a Shannon entropy function, and $X_a$ and $X_b$ are random variables representing voxel intensities in image patches A and B, respectively.

6. The method of claim 1, wherein generating a synthesized target modality medical image by selecting, jointly for all of the plurality of voxels in the target modality medical image, intensity values from the multiple candidate target modality intensity values generated for each of the plurality of voxels comprises:

selecting best candidate target modality intensity values for all of the plurality of voxels of the target modality medical image jointly by simultaneously maximizing a global mutual information cost and minimizing a local spatial consistency cost.

7. The method of claim 6, wherein selecting best candidate target modality intensity values for all of the plurality of voxels of the target modality medical image jointly by simultaneously maximizing a global mutual information cost and minimizing a local spatial consistency cost comprises:

calculating weighting parameters for the multiple candidate target modality intensity values generated for each of the plurality of voxels of the target modality medical image that optimize a cost function that combines the global mutual information cost and the local spatial consistency cost.

8. The method of claim 7, wherein selecting best candidate target modality intensity values for all of the plurality of voxels of the target modality medical image jointly by simultaneously maximizing a global mutual information cost and minimizing a local spatial consistency cost further comprises:

selecting, for each of the plurality of voxels of the target modality medical image, a candidate target modality intensity value having a maximum weighting parameter among the multiple candidate target modality intensity values generated for that voxel.

9. The method of claim 7, wherein selecting best candidate target modality intensity values for all of the plurality of voxels of the target modality medical image jointly by simultaneously maximizing a global mutual information cost and minimizing a local spatial consistency cost further comprises:

selecting, for each of the plurality of voxels of the target modality medical image, an intensity value equal to an average of a number of candidate target modality intensity values having a having highest weighting parameters among the multiple candidate target modality intensity values generated for that voxel.

10. The method of claim 7, wherein selecting best candidate target modality intensity values for all of the plurality of voxels of the target modality medical image jointly by simultaneously maximizing a global mutual information cost and minimizing a local spatial consistency cost further comprises:

initializing all of the weighting parameters for the candidate target modality intensity values generated for each of the plurality of voxels of the target modality training image with a value of $$\frac{1}{K}$$

prior to calculating the weighting parameters that optimize the cost function, where K is a number of candidate target modality intensity values generated for each of the plurality of voxel of the target modality training image.

11. The method of claim 1, further comprising:
refining the synthesized the synthesized target modality image using coupled sparse representation.

12. The method of claim 11, wherein refining the synthesized the synthesized target modality image using coupled sparse representation comprises:

extracting a plurality of source image patches the source modality medical image and a plurality of target image patches from the synthesized target modality medical image, wherein corresponding pairs of the source and target image patches are centered at same voxel locations in the source modality medical image and the synthesized target modality medical image;

jointly learning a source modality dictionary, a target modality dictionary, and coupled sparse code for the corresponding pairs of the source and target image patches at each voxel location in the source modality medical image and the synthesized target modality medical image based on the plurality of source image patches and the plurality of target image patches;

reconstructing each of the plurality of target image patches using the learned target modality dictionary and the learned coupled sparse code for the voxel location at which the target image patch is centered; and modifying the intensity value of each voxel in the synthesized target modality medical image to match an intensity value of a center voxel of the reconstructed target image patch centered at that voxel location.

13. The method of claim 12, wherein jointly learning a source modality dictionary, a target modality dictionary, and coupled sparse code for the corresponding pairs of the source and target image patches at each voxel location in the source modality medical image and the synthesized target modality medical image based on the plurality of source image patches and the plurality of target image patches comprises:

optimizing an objective function: minimize$_{D_s,D_t,\{\alpha_v\}} \Sigma_{v \in V}$ ($\|P_v^s - D_s \alpha_v\|_2^2 + \|P_v^t - D_t \alpha_v\|_2^2$) subject to $\|\alpha_v\|_0 \leq T_0 \forall v \in V$ using a K-SVD algorithm, where $P_v^s$ and $P_v^t$ denote the source and target image patches centered at voxel v extracted from the source modality medical image $I_s$ and the synthesized target modality medical image $I_t$, respectively, $D_s$ and $D_t$ are the source and target dictionaries, respectively, $\alpha_v$ is the coupled sparse code for the corresponding pair of source and target image patches $P_v^s$ and $P_v^t$, $T_0$ is a sparsity parameter, and V refers to a set of voxel locations.

14. An apparatus for unsupervised cross-modal synthesis of a target modality medical image from a source modality medical image, comprising:
   means for receiving the source modality medical image;
   means for generating multiple candidate target modality intensity values for each of a plurality of voxels of the target modality medical image based on corresponding voxels in the source modality medical image; and
   means for generating a synthesized target modality medical image by selecting, jointly for all of the plurality of voxels in the target modality medical image, intensity values from the multiple candidate target modality intensity values generated for each of the plurality of voxels.

15. The apparatus of claim 14, wherein the means for generating multiple candidate target modality intensity values for each of a plurality of voxels of the target modality medical image based on corresponding voxels in the source modality medical image comprises:
   means for generating the multiple candidate target modality intensity values for each of the plurality of voxels independently using a cross-modal nearest neighbor search between a corresponding portion of the source modality medical image and a plurality of target modality training images.

16. The apparatus of claim 14, wherein the means for generating multiple candidate target modality intensity values for each of a plurality of voxels of the target modality medical image based on corresponding voxels in the source modality medical image comprises:
   means for extracting from the source modality medical image a plurality of image patches, each centered at a respective one of a plurality of voxels of the source modality medical image;
   means for obtaining, for each of the plurality of image patches extracted from the source modality medical image, K nearest image patches from a plurality of target modality training images using a cross-modal nearest neighbor search based on a cross-modal similarity measure between the image patches extracted from the source modality medical image and image patches of the target modality training images; and
   means for generating, for each of the plurality of image patches extracted from the source image, K candidate target modality intensity values for a corresponding set of voxels in the target modality medical image using intensity values of a corresponding set of voxels in each of the K nearest image patches from the plurality of target modality training images, wherein the corresponding set of voxels in the target modality medical image includes a voxel corresponding to the voxel at which the image patch extracted from the source image is centered and neighboring voxels and the corresponding set of voxels in each of the K nearest image patches includes a center voxel and neighboring voxels in each of the K nearest image patches.

17. The apparatus of claim 16, wherein the cross-modal similarity measure between the image patches extracted from the source modality medical image and the image patches of the target modality training images is a voxel intensity-based mutual information measure.

18. The apparatus of claim 14, wherein the means for generating a synthesized target modality medical image by selecting, jointly for all of the plurality of voxels in the target modality medical image, intensity values from the multiple candidate target modality intensity values generated for each of the plurality of voxels comprises:
   means for selecting best candidate target modality intensity values for all of the plurality of voxels of the target modality medical image jointly by simultaneously maximizing a global mutual information cost and minimizing a local spatial consistency cost.

19. The apparatus of claim 18, wherein the means for selecting best candidate target modality intensity values for all of the plurality of voxels of the target modality medical image jointly by simultaneously maximizing a global mutual information cost and minimizing a local spatial consistency cost comprises:
   means for calculating weighting parameters for the multiple candidate target modality intensity values generated for each of the plurality of voxels of the target modality medical image that optimize a cost function that combines the global mutual information cost and the local spatial consistency cost.

20. The apparatus of claim 14, further comprising:
   means for refining the synthesized the synthesized target modality image using coupled sparse representation.

21. The apparatus of claim 20, wherein the means for refining the synthesized the synthesized target modality image using coupled sparse representation comprises:
   means for extracting a plurality of source image patches the source modality medical image and a plurality of target image patches from the synthesized target modality medical image, wherein corresponding pairs of the source and target image patches are centered at same voxel locations in the source modality medical image and the synthesized target modality medical image;
   means for jointly learning a source modality dictionary, a target modality dictionary, and coupled sparse code for the corresponding pairs of the source and target image patches at each voxel location in the source modality medical image and the synthesized target modality medical image based on the plurality of source image patches and the plurality of target image patches;
   means for reconstructing each of the plurality of target image patches using the learned target modality dictionary and the learned coupled sparse code for the voxel location at which the target image patch is centered; and
   means for modifying the intensity value of each voxel in the synthesized target modality medical image to match an intensity value of a center voxel of the reconstructed target image patch centered at that voxel location.

22. A non-transitory computer readable medium storing computer program instructions for unsupervised cross-modal synthesis of a target modality medical image from a source modality medical image, the computer program instructions when executed by a processor cause the processor to perform operations comprising:
   receiving the source modality medical image;
   generating multiple candidate target modality intensity values for each of a plurality of voxels of the target modality medical image based on corresponding voxels in the source modality medical image; and generating a synthesized target modality medical image by selecting, jointly for all of the plurality of voxels in the target modality medical image, intensity values from the multiple candidate target modality intensity values generated for each of the plurality of voxels.

23. The non-transitory computer readable medium of claim 22, wherein generating multiple candidate target modality intensity values for each of a plurality of voxels of the target modality medical image based on corresponding voxels in the source modality medical image comprises:

generating the multiple candidate target modality intensity values for each of the plurality of voxels independently using a cross-modal nearest neighbor search between a corresponding portion of the source modality medical image and a plurality of target modality training images.

24. The non-transitory computer readable medium of claim 22, wherein generating multiple candidate target modality intensity values for each of a plurality of voxels of the target modality medical image based on corresponding voxels in the source modality medical image comprises:

extracting from the source modality medical image a plurality of image patches, each centered at a respective one of a plurality of voxels of the source modality medical image;

obtaining, for each of the plurality of image patches extracted from the source modality medical image, K nearest image patches from a plurality of target modality training images using a cross-modal nearest neighbor search based on a cross-modal similarity measure between the image patches extracted from the source modality medical image and image patches of the target modality training images; and generating, for each of the plurality of image patches extracted from the source image, K candidate target modality intensity values for a corresponding set of voxels in the target modality medical image using intensity values of a corresponding set of voxels in each of the K nearest image patches from the plurality of target modality training images, wherein the corresponding set of voxels in the target modality medical image includes a voxel corresponding to the voxel at which the image patch extracted from the source image is centered and neighboring voxels and the corresponding set of voxels in each of the K nearest image patches includes a center voxel and neighboring voxels in each of the K nearest image patches.

25. The non-transitory computer readable medium of claim 24, wherein the cross-modal similarity measure between the image patches extracted from the source modality medical image and the image patches of the target modality training images is a voxel intensity-based mutual information measure.

26. The non-transitory computer readable medium of claim 22, wherein generating a synthesized target modality medical image by selecting, jointly for all of the plurality of voxels in the target modality medical image, intensity values from the multiple candidate target modality intensity values generated for each of the plurality of voxels comprises:

selecting best candidate target modality intensity values for all of the plurality of voxels of the target modality medical image jointly by simultaneously maximizing a global mutual information cost and minimizing a local spatial consistency cost.

27. The non-transitory computer readable medium of claim 26, wherein selecting best candidate target modality intensity values for all of the plurality of voxels of the target modality medical image jointly by simultaneously maximizing a global mutual information cost and minimizing a local spatial consistency cost comprises:

calculating weighting parameters for the multiple candidate target modality intensity values generated for each of the plurality of voxels of the target modality medical image that optimize a cost function that combines the global mutual information cost and the local spatial consistency cost.

28. The non-transitory computer readable medium of claim 27, wherein selecting best candidate target modality intensity values for all of the plurality of voxels of the target modality medical image jointly by simultaneously maximizing a global mutual information cost and minimizing a local spatial consistency cost further comprises:

selecting, for each of the plurality of voxels of the target modality medical image, a candidate target modality intensity value having a maximum weighting parameter among the multiple candidate target modality intensity values generated for that voxel.

29. The non-transitory computer readable medium of claim 27, wherein selecting best candidate target modality intensity values for all of the plurality of voxels of the target modality medical image jointly by simultaneously maximizing a global mutual information cost and minimizing a local spatial consistency cost further comprises:

selecting, for each of the plurality of voxels of the target modality medical image, an intensity value equal to an average of a number of candidate target modality intensity values having a having highest weighting parameters among the multiple candidate target modality intensity values generated for that voxel.

30. The non-transitory computer readable medium of claim 27, wherein selecting best candidate target modality intensity values for all of the plurality of voxels of the target modality medical image jointly by simultaneously maximizing a global mutual information cost and minimizing a local spatial consistency cost further comprises:

initializing all of the weighting parameters for the candidate target modality intensity values generated for each of the plurality of voxels of the target modality training image with a value of $$\frac{1}{K}$$

prior to calculating the weighting parameters that optimize the cost function, where K is a number of candidate target modality intensity values generated for each of the plurality of voxel of the target modality training image.

31. The non-transitory computer readable medium of claim 22, wherein the operations further comprise:

refining the synthesized the synthesized target modality image using coupled sparse representation.

32. The non-transitory computer readable medium of claim 31, wherein refining the synthesized the synthesized target modality image using coupled sparse representation comprises:

extracting a plurality of source image patches the source modality medical image and a plurality of target image patches from the synthesized target modality medical image, wherein corresponding pairs of the source and target image patches are centered at same voxel locations in the source modality medical image and the synthesized target modality medical image;
jointly learning a source modality dictionary, a target modality dictionary, and coupled sparse code for the corresponding pairs of the source and target image patches at each voxel location in the source modality medical image and the synthesized target modality medical image based on the plurality of source image patches and the plurality of target image patches;
reconstructing each of the plurality of target image patches using the learned target modality dictionary and the learned coupled sparse code for the voxel location at which the target image patch is centered; and
modifying the intensity value of each voxel in the synthesized target modality medical image to match an intensity value of a center voxel of the reconstructed target image patch centered at that voxel location.

* * * * *